United States Patent [19]

Schreiber et al.

[11] 4,129,569
[45] Dec. 12, 1978

[54] CYCLIC OXAZO DERIVATIVES

[75] Inventors: William L. Schreiber, Jackson; James N. Siano, Keyport; John B. Hall, Rumson, all of N.J.

[73] Assignee: International Flavors & Fragrances Inc., New York, N.Y.

[21] Appl. No.: 807,057

[22] Filed: Jun. 16, 1977

[51] Int. Cl.² .................. C07D 263/04; C07D 265/06
[52] U.S. Cl. ........................... 260/307 FA; 252/522; 544/88; 260/586 R; 260/586 F; 260/593 R
[58] Field of Search .................... 544/88; 260/307 FA

[56] References Cited

U.S. PATENT DOCUMENTS 2,960,508  11/1960  Croxall et al. .................. 260/307
2,974,140  3/1971  Croxall et al. .................. 260/244

FOREIGN PATENT DOCUMENTS 2143563  3/1973  France.
48-08049  7/1972  Japan.

OTHER PUBLICATIONS

Ishino et al. - J. Org. Chem. 39, (1), 1974.
Stoll et al. - Hew. Chim. Acta. 38, 1593 (1955).
Kato et al. - Bull. Chem. Soc. Jap. 1971, 44(12), 3437-3439.

Primary Examiner—Raymond V. Rush
Attorney, Agent, or Firm—Arthur L. Liberman; Franklin D. Wolffe; Harold Haidt

[57] ABSTRACT

Described are intermediate mixtures of cyclic oxazo derivatives having the generic structure:

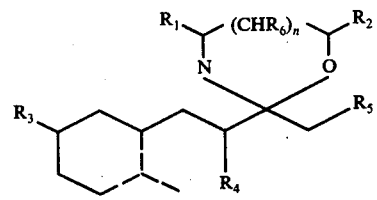

wherein one of the dashed lines is a carbon carbon double bond and the other two dashed lines are carbon carbon single bonds and n is 0 or 1; $R_1$, $R_2$ and $R_6$ are each the same or different and each represents hydrogen or $C_1$-$C_3$ lower alkyl; and $R_3$, $R_4$ and $R_5$ are each the same or different and each represents hydrogen or methyl; as well as the precursor oxazo derivative having the structure:

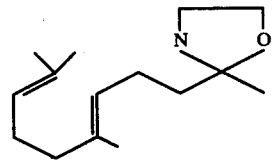

Such oxazo derivatives have as their primary use intermediates in reactions whereby mixtures of dihydro alpha ionone, dihydro beta ionone and dihydro gamma ionone or homologues thereof are produced.

3 Claims, 3 Drawing Figures

FIG.1 NMR SPECTRUM ACCORDING TO EXAMPLE I (A)

EXAMPLE I(A)

GLC PROFILE

EXAMPLE I(B)
CAPILLARY G.C.

CYCLIC OXAZO DERIVATIVES

BACKGROUND OF THE INVENTION

The present invention relates to dihydro gamma ionone and homologues thereof and mixtures of dihydro alpha ionone, dihydro beta ionone and dihydro gamma ionone and alkyl homologues thereof produced by a novel process, as well as the intermediates used in said novel process. Dihydro alpha ionone, dihydro beta ionone and dihydro gamma ionone and homologues thereof are useful in augmenting and/or enhancing the flavor and/or aroma of consumable materials such as foodstuffs, tobaccos, perfumes, colognes and perfumed articles.

Prior to our invention, dihydro gamma ionone was produced by means of a method such as that described in British Pat. No. 794,416 published on May 7, 1958. That is, alpha ionone is reduced in the presence of Raney nickel to form dihydro-alpha-ionone. The dihydro-alpha-ionone is then reduced with lithium aluminum hydride to form dihydro-alpha-ionol. The dihydro-alpha-ionol is then acetylated to form dihydro-alpha-ionol acetate. Hydrogen chloride is added to the resulting dihydro-alpha-ionol acetate thus yielding 3-chloro-tetrahydroionyl acetate. The 3-chloro-tetrahydroionyl acetate is then treated with potassium laurate thereby producing a mixture of dihydro gamma-ionyl acetate, dihydro alpha-ionyl acetate and dihydro-beta-ionyl acetate. The resulting mixture of dihydro ionyl acetates is then saponified to the corresponding alcohols. This mixture of alcohols is then oxidized with such oxidizing agents as chromic acid to yield a mixture of dihydro ionones, dihydro alpha ionone, dihydro beta ionone and dihydro gamma ionone.

Dihydro gamma ionone is a constituent of ambergris. It has a warm, woody, earthy aroma; the alpha isomer on the other hand has a sweet, floral, woody note. The mixture of dihydro ionones produced according to British Pat. No. 794,416 has a woody, ionone like, floral, sweet, fruity and bitter flavor profile. In addition to dihydro gamma ionone being used in fragrances as part of an ambergris replacement, dihydro gramma ionone is also useful for cyclization to "ambrinol" in high yield.

Accordingly, a need has arisen in the perfumery and flavor industries for an efficient and inexpensive method for producing dihydro gamma ionone and homologues thereof as well as mixtures containing dihydro gamma ionone or homologues thereof, dihydro beta ionone or homologues thereof and dihydro alpha ionone or homologues thereof, respectively. Our invention has fulfilled that need.

The protection of a carbonyl functional group during hydration or cyclization using nitrogen containing protecting groups for the carbonyl function is well known in the prior art. Thus, Ogawa, et al. in Japanese Pat. No. 7,208,049 and French Pat. No. 2,146,563 discloses a process for preparing hydroxy citronellal by treating citronellal with a primary or secondary aliphatic amine or amino alcohol, hydrating the adduct with aqueous acid and hydrolyzing the resulting imine or immonium group using a base. One of the products formed in situ is the oxazolidine intermediate. This is disclosed in detail on page 109, J. Org. Chem., Volume 39, No. 1, 1974 at Scheme 2.

Cyclization of gamma dihydro ionone to ambrinol according to the reaction using boron trifluoride etherate is known in the prior art: M. Stoll and M. Hinder, Helv. Chem. Acta., 38, 1593 (1955).

A reaction is described by Stoll, Helv. Chim. Acta 38, 1587–92 (1955). U.S. Pat. No. 2,933,506 issued on Apr. 19, 1960 describes the reaction:

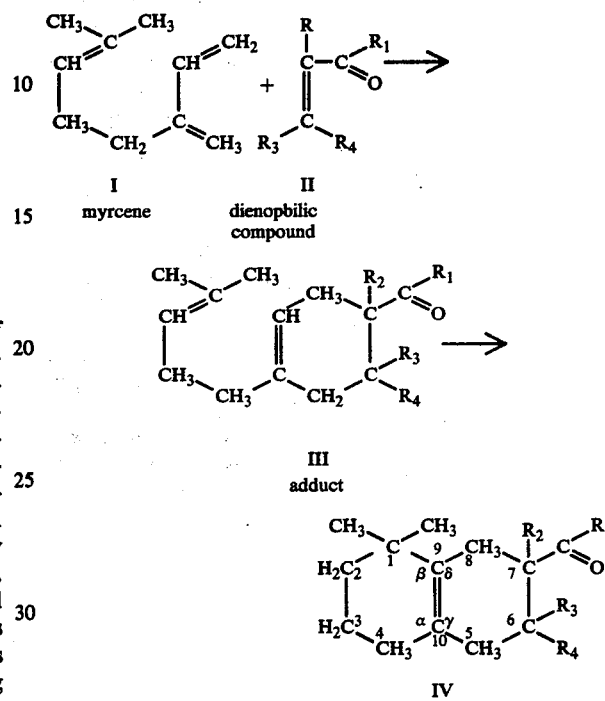

At Column 3, Lines 39–47 it is stated that when using a myrcene adduct according to Formula III, which is an aldehyde characterized by having a hydrogen atom at $R_1$ (while $R_2$, $R_3$ and $R_4$ may also be hydrogen or may be substituted by other organic groups), the carbonyl group is preferably protected from the action of the acid cyclization reagent. For this purpose it is stated that the aldehyde group is advantageously and temporarily converted into the azomethine group by condensing the aldehyde with an amine such as an aromatic amine such as aniline. It is further stated at lines 49–57 that following cyclization of the myrcene adduct of Formula III with the protected aldehyde group, the entire reaction mixture is blown with steam for a few minutes whereby the Shiff base is split up into the cyclic aldehyde of Formula IV and the amine used for protection.

However, notwithstanding the disclosures of the prior art nothing in the prior art even implicitly indicates the production of dihydro gamma ionone and homologues thereof according to the low cost efficient process of our invention.

THE INVENTION

Figure 1:
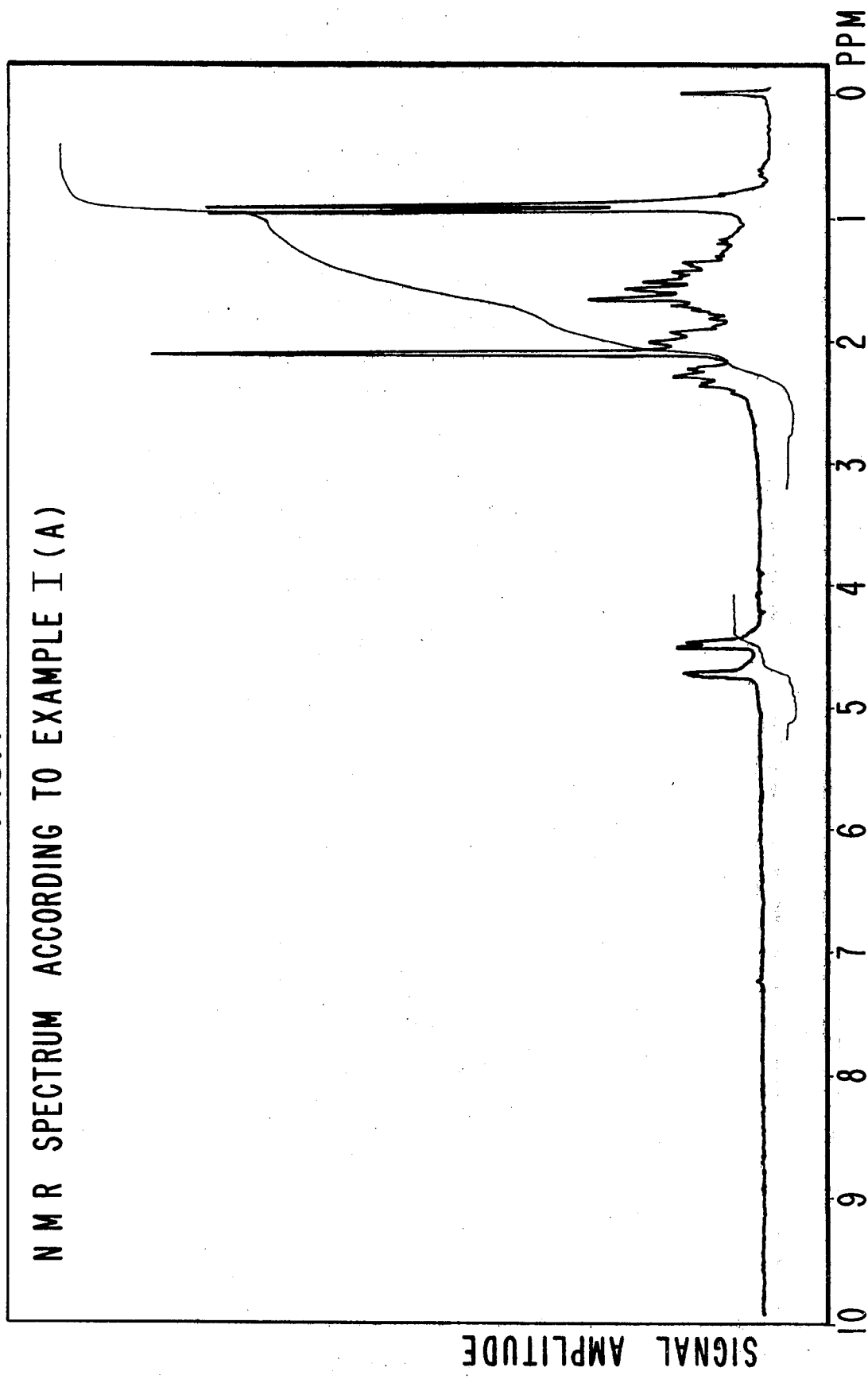
FIG. 1 is the NMR spectrum for the gamma dihydro ionone of Example 1A which has been purified by preparative GLC trapping.

This invention relates to the preparation of dihydro gamma ionone and mixtures containing dihydro gamma ionone, dihydro alpha ionone and dihydro beta ionone and homologues thereof which are useful ingredients for foodstuff flavorants, foodstuff flavor enhancers, tobacco flavorant, tobacco flavor modifiers, perfumes, perfumed articles and cosmetics. More particularly, this invention has to do with a process for the preparation of dihydro gamma ionone and mixtures containing dihydro alpha ionone, dihydro beta ionone and dihydro gamma ionone and homologues thereof for use in perfumery or in foodstuff or tobacco flavoring by means of a three step process which renders the preparation of such compounds commercially feasible and inexpensive. This invention also covers novel intermediates used in such process.

The process of our invention involves, firstly, the reaction of geranyl acetone or a homologue of geranyl acetone with an amino alcohol thereby forming a cyclic oxazo derivative of said geranyl acetone whereby the ketone moiety of the geranyl acetone is "protected." This reaction is illustrated as follows:

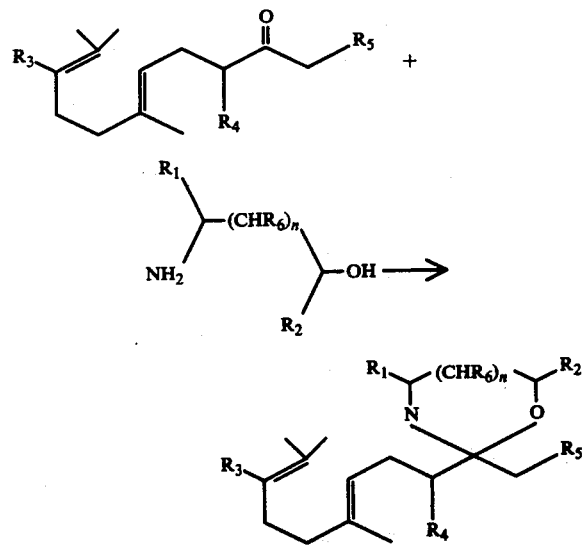

wherein n is 0 or 1, $R_1$, $R_2$ and $R_6$ are the same or different and each represents hydrogen or $C_1$–$C_3$ lower alkyl, and $R_3$, $R_4$ and $R_5$ are the same or different and each represents hydrogen or methyl. The second step of the process of our invention concerns the reaction of the cyclic oxazo derivative of geranyl acetone or one of its homologues whereby a cyclization takes place thereby causing the formulation of the mixture of dihydro gamma ionone cyclic oxazo derivative, dihydro alpha ionone cyclic oxazo derivative and dihydro beta ionone cyclic oxazo derivative or homologues thereof, wherein two of the dashed lines represent carbon-carbon single bonds and the other of the dashed lines represents a carbon-carbon double bond and n, $R_1$, $R_2$, $R_3$, $R_4$, $R_5$ and $R_6$ are as defined above. This cyclization is accomplished using a Lewis acid catalyst; preferably a boron trifluoride complex catalyst, for example boron trifluoride diethyl etherate or $BF_3$ itself.

This reaction is illustrated as follows:

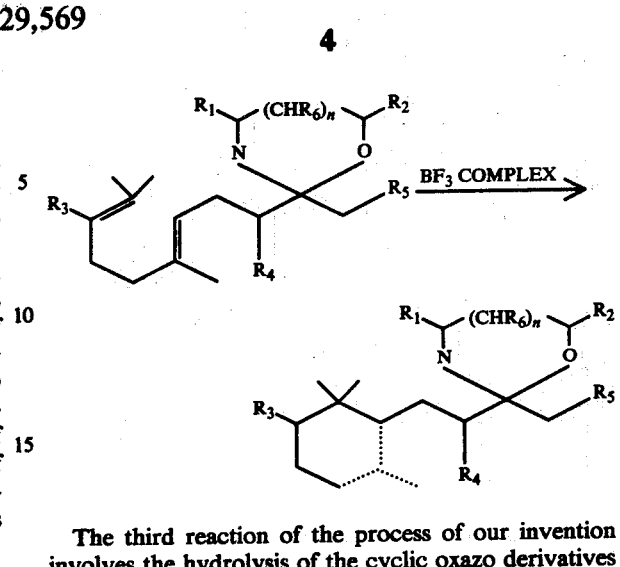

The third reaction of the process of our invention involves the hydrolysis of the cyclic oxazo derivatives of the dihydro gamma, alpha and beta ionone mixture whereby the dihydro gamma, alpha and beta ionone mixture is produced; or it involves the hydrolysis of the mixture of cyclic oxazo derivatives of the dihydro gamma ionone homologue. The dihydro alpha ionone homologue and the dihydro beta ionone homologue. This reaction is illustrated as follows:

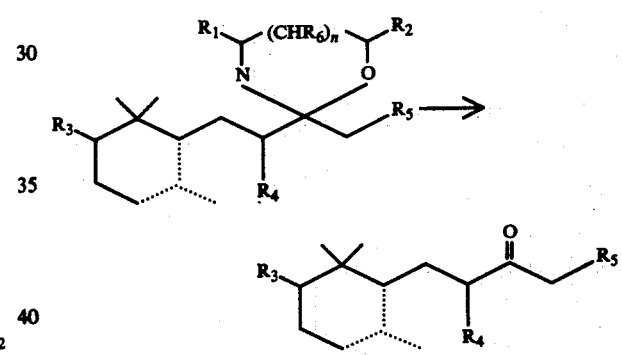

The aforementioned reactions are more specifically illustrated as follows, wherein $R_3$, $R_4$, $R_5$ and $R_6$ are each hydrogen:

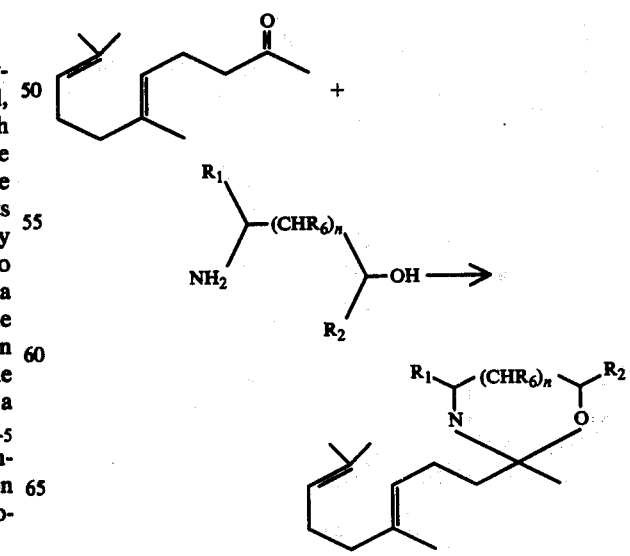

-continued

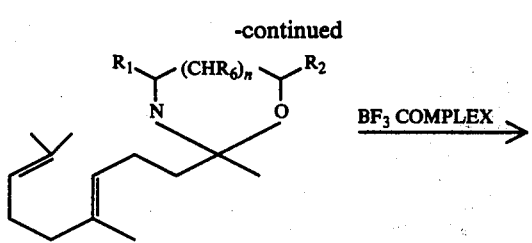

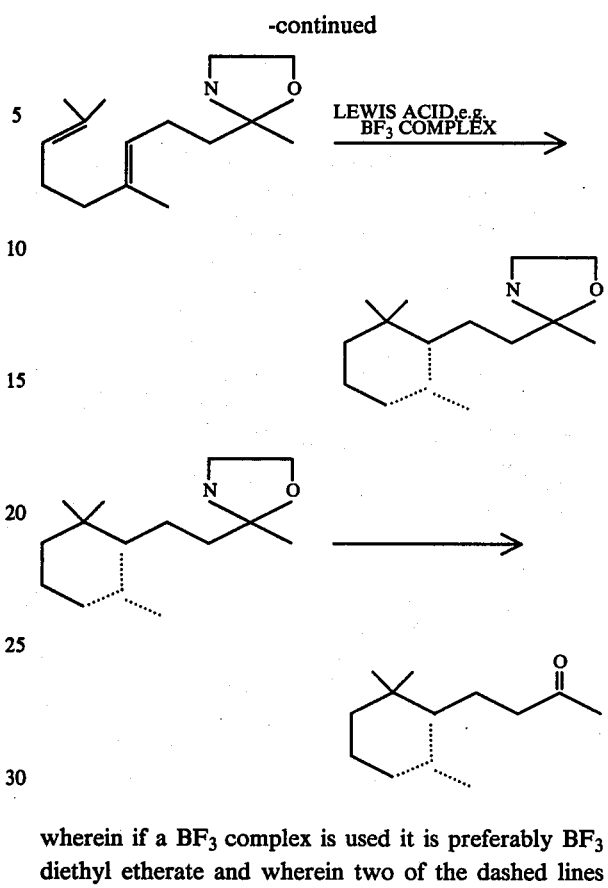

wherein $R_1$ and $R_2$ are the same or different hydrogen or lower alkyl; and wherein n is 0.

In producing mixtures of dihydro gamma ionone, dihydro alpha ionone and dihydro beta ionone or, in producing dihydro gamma ionone per se, using 2-aino ethanol and geranyl acetone as the starting materials, the following reaction sequence is employed:

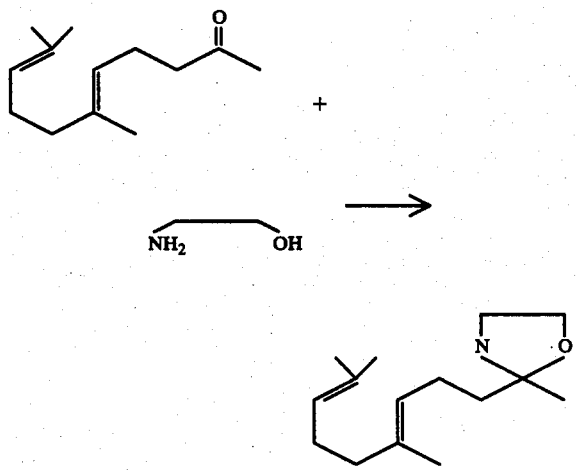

wherein if a $BF_3$ complex is used it is preferably $BF_3$ diethyl etherate and wherein two of the dashed lines represent a carbon-carbon single bond, the other of the dashed lines represents a carbon-carbon double bond.

The novel genus of intermediates (cyclic oxazo derivatives of ketones) of our invention are set forth, generically, as follows:

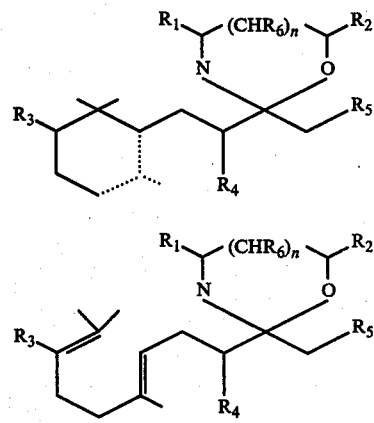

wherein one of the dashed lines is a carbon-carbon double bond and the other two dashed lines are carbon-carbon single bonds; n is zero or one; $R_1$, $R_2$ and $R_6$ are the same or different and each represents hydrogen or $C_1$–$C_3$ lower alkyl; and $R_3$, $R_4$ and $R_5$ are the same or different and each represents hydrogen or methyl. Other more specific representations of the novel intermediates of our invention are as follows:

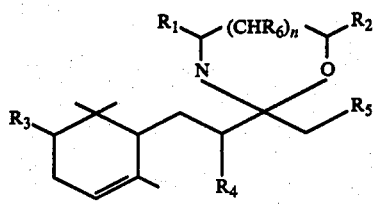 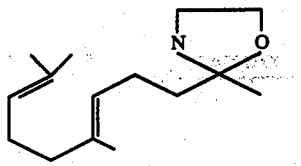
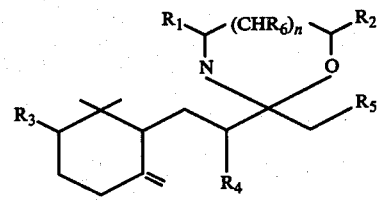 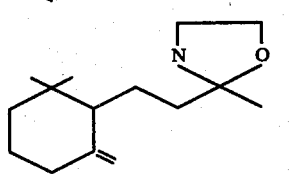
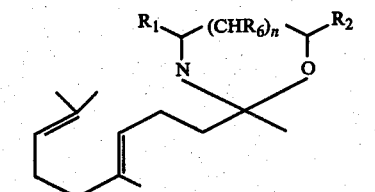 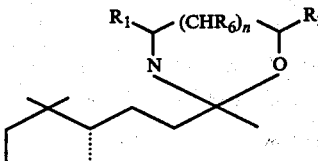
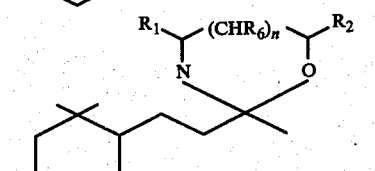 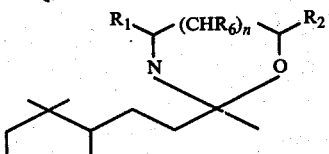
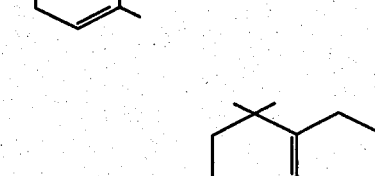 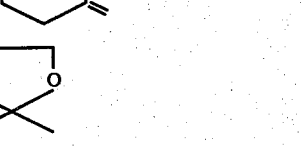
Insofar as the reaction of the alkanolamine with the geranyl acetone or the homologue of geranyl acetone is concerned, to wit, the reaction;
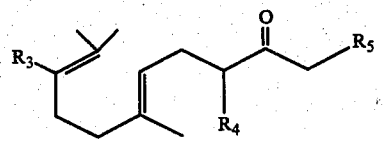 +
-continued
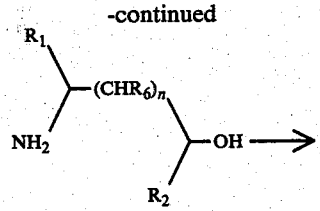 →

-continued

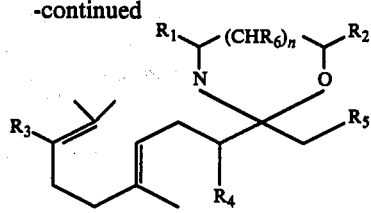

it is preferable to carry out this reaction at a temperature in the range of from about 80° C up to about 140° C. It is also preferable to carry out this reaction in a solvent at reflux in order to remove water of reaction azeotropically. The yield of cyclic oxazo derivative is a function of the time of reaction; and the time of reaction preferably is from 1 up to 10 hours. Any inert solvent capable of azeotropically removing water can be used in this first reaction. A preferred solvent is toluene but it is to be understood that the process of our invention is not restricted to the use of toluene.

The reaction involving the cyclization of the oxazo derivative of geranyl acetone or the oxazo derivative of the geranyl acetone homologue is preferably carried out at a temperature in the range of from about 0° C up to about 40° C. The Lewis Acid cyclization agent used is preferably a boron trifluoride complex which is preferably boron trifluoride diethyl ether complex. The reaction is preferably carried out using an amount of boron trifluoride complex or other Lewis Acid of from 1.20 up to 3.0 molar equivalents for each mole of cyclic oxazo derivative present Boron trifluoride gas (uncomplexed) is another example of a preferred Lewis Acid useful in our invention.

The reaction concerning the hydrolysis of the cycle oxazo derivative of the dihydro gamma ionone — dihydro alpha ionone — dihydro beta ionone mixture, or the mixture of homologues of the cyclic oxazo derivative of the dihydro gamma ionone — dihydro beta ionone — dihydro alpha ionone mixture is carried out by gradually neutralizing the Lewis Acid which is present by adding one molar equivalent of an aqueous base such as sodium acetate, sodium hydroxide or other alkali alkanoates, hydroxides or carbonates. The reaction temperature in the final hydrolysis should be maintained at between 0° C and 50° C with a preferable temperature range of 20°-30° C.

Although all reactions are preferably and most conveniently carried out at atmospheric pressure superatmospheric pressures or subatmospheric pressures may be used. However, the temperature ranges of reaction should be maintained within those ranges set forth above.

The mixtures of dihydro ionones as produced above may by greatly enriched in the gama isomer by fractional distillation (See Example I(A). Pure dihydro gamma ionone may be then isolated, if desired, by preparative GLC trapping.

In general the dihydro gamma ionone and mixtures of dihydro gamma ionone, dihydro beta ionone and dihydro alpha ionone as well as the homologues thereof produced according to the process of our invention were not previously capable of being prepared by means of cyclization. Previously, such cyclization would have been carried out under acidic conditions on geranyl acetone derivatives causing the carbonyl group to participate in the cyclization thus yielding products other than dihydro ionones. In the present invention the cyclic oxazo moiety is stable to the cyclization reaction conditions and effectively inactivates the carbonyl group so that the desired cyclization may occur. This is considered to be a significant improvement over the multistep processes described in the literature.

The reaction product mixtures containing the dihydro gamma ionone, dihydro beta ionone and dihydro alpha ionone as well as the specific ionone isomers produced according to the process of our invention are clear liquids with intense and persistent warm, woody and earthy notes important in creating amber aromas. The materials produced according to the process of our invention are particularly suited to use as perfume materials in the preparation of perfume compositions. They are very suited to perfumery wherein an amber or woody — amber aroma is required. To make such an amber or woody — amber type of perfume, the materials of this invention can be combined with "auxilary perfume adjuvants" including one or more of many types of odor materials such as bergamot oil, vetivert oil, patchouli oil, sandalwood oil, oakmoss and floral musk. The materials produced according to the novel process of our invention can also be combined with the customary auxiliary perfume adjuvants such as natural essential oils, synthetic essential oils, aldehydes, other ketones, carboxylic acid esters, aryl alcohols, alkanols, lactones, saturated hydrocarbons, unsaturated hydrocarbons, fixatives, solvents, dispersants, surface active agents, aerosol propellants, and the like.

The following examples serve to illustrate embodiments of our invention as it is now preferred to practice it. It will be understood that these examples are illustrative and the invention is to be considered restricted thereto only as indicated in the appended claims.

EXAMPLE I(A)

PREPARATION OF DIHYDRO IONONE - ALPHA, BETA AND GAMMA ISOMER MIXTURE

Reactions

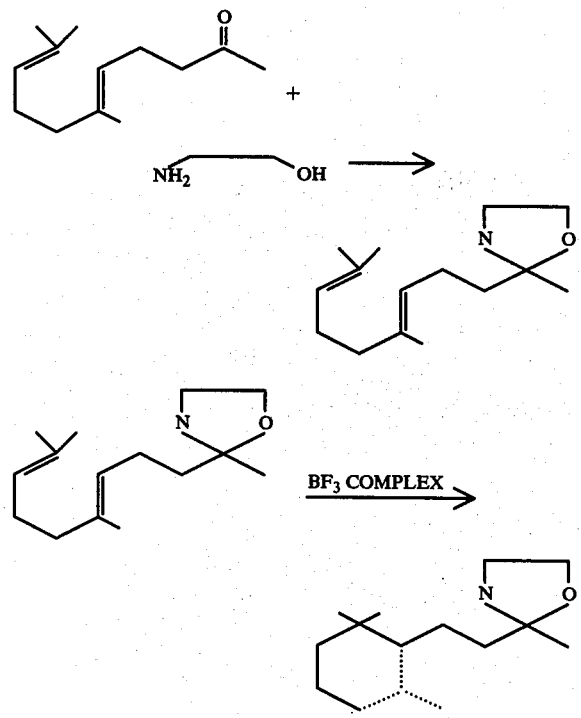

-continued

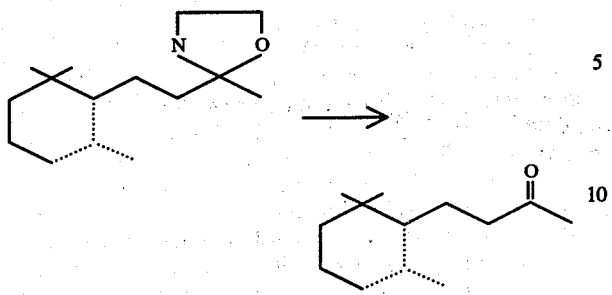

A 12 liter reaction vessel equipped with stirrer, thermometer, Dean-Stark trap, and condenser is charged with 2838g (14.6 moles) geranyl acetone, 1112g (18.2 moles) ethanolamine and 2838g toluene. The mixture is refluxed rapidly with water separation until water evolution is very slow (less than 8 ml/hr). The mass is cooled to 25° C and stirred well as 4155g (29.3 moles) boron trifluoride etherate is added over a 1 hour period. The reaction mixture is stirred at 25° C for 20 hours.

The mixture is maintained at 20°–30° C with a cooling bath as a solution of 2399g (29.3 moles) of sodium acetate in 8 liters water is added. The aqueous lqyer is removed and the organic layer is washed successively with water and aqueous sodium bicarbonate. The organic phase is then distilled from 145g triethanolamine without fractionation to remove solvent and separate the product from non volatile residue. The material is then fractionally distilled to give 1828g of material boiling point 90°–94° C (2.8 mm) which contains approximately 50% dihydro gamma ionone, the remainder being largely dihydro alpha and beta isomers.

The dihydro ionone derivative mixture produced according to this example is used as indicated in Example III as a constituent of an amber perfume formulation.

Figure 2:
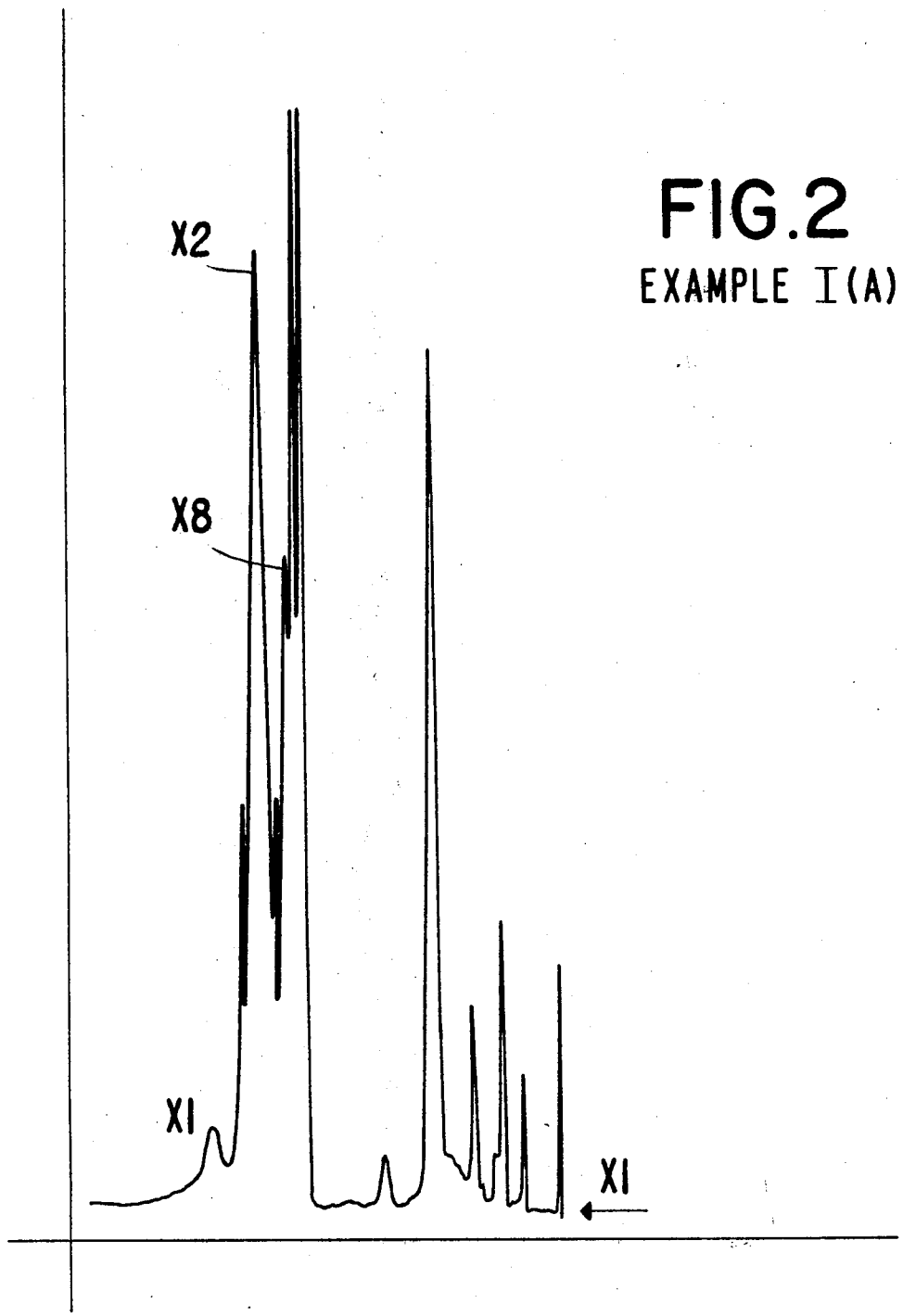
FIG. 2 is the GLC profile for the reaction product of Example 1A containing the high proportion of dihydro gamma ionone.

A sample of the pure gamma isomer is obtained by preparative GLC trapping. FIG. 1 is the NMR (Nuclear Magnetic Resonance) spectrum of this purified isomer. FIG. 2 is the GLC profile of the above distilled material.

The product may be greatly enriched in the gamma isomer by fractional distillation. Thus redistillation of the above product through a 2 ft. × 1½ in. Goodloe packed column at a 19:1 reflux ratio gives 458g of material which contains 87% gamma dihydro ionone, b.p. 100°–103° (4.0 mm).

EXAMPLE I(B)

To a 22 liter 3 neck flask fitted with thermometer, stirrer, Dean-St rk trap and condenser is added 4268g (22.0 moles) geranyl acetone, 1610g (26.4 moles) ethanolamine (Aldrich Chemical Co.) and 4200 ml toluene. The mixture is heated to rapid reflux with water separation for 8 hours. The mixture is then cooled to 20°–25° C as 5467g (40.0 moles) boron trifluoride etherate is added. The mass is aged for 20 hours at room temperature. A slurry of 3280g sodium acetate and 3280ml water is added to this reaction mixture while it is stirred at 15°–25° C. More water is added to dissolve salts and the aqueous layer is separated. The organic layer is washed with water and then with aqueous sodium bicarbonate. The organic layer is rapidly distilled to remove solvent and free the product from residue. The material is then fractionally distilled through a 2 ft. × 1½in. Goodloe packed column to give 1678g of product, b.p. 89–96° C (2.3–2.9 mm), which contains (by GC area normalization) 66% dihydro gamma ionone, 26% dihydro alpha ionone and 5.5% dihydro beta ionone (See FIG. 3).

Figure 3:
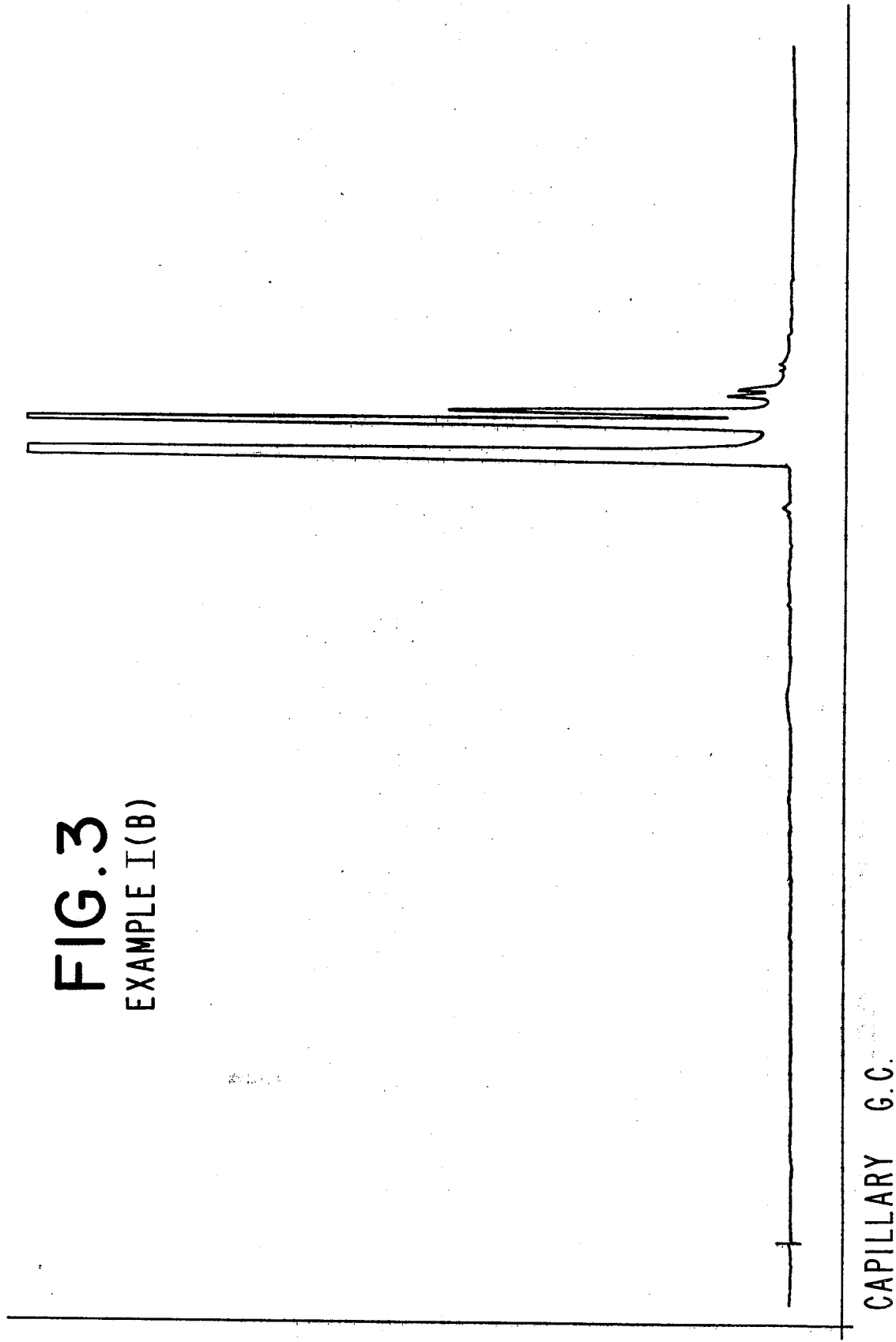
FIG. 3 is a capillary GC profile for the reaction product of Example 1B.

FIG. 3 is a capillary GC profile for the reaction product of Example 1(B) conditions — 500 ft. × 0.03 in. Carbowax 20M Column; 80°– 180° C at 2°/min.).

EXAMPLE II

PREPARATION OF COLOGNE AND HANDKERCHIEF PERFUME

The reaction product of Example I(A) is incorporated into a cologne having a concentration of 2.5% in 80% aqueous ethanol; and into a handkerchief perfume in a concentration of 20% (in 95% ethanol). The use of the reaction product of Example I(A) affords a distinct and definite warm, woody, earthy aroma to the handkerchief perfume and to the cologne.

EXAMPLE III

PREPARATION OF PERFUME COMPOSITION

The following perfume composition is prepared by admixing the following ingredients in the indicated proportions:

| Ingredient | Amount (Grams) |
| --- | --- |
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petitgrain SA | 20 |
| Bergamot Oil | 30 |
| Alpha Methyl Ionone | 25 |
| Mixture of isomers of 1', 2', 3', 4', 5', 6', 7', 8'-octahydro-2', 3', 8', 8'-tetramethyl-2'-acetonaphthones produced by the process of Example II (prior to GLC separation) of U.S. Pat. No. 3,911,018 | 10 |
| Cyclized Bicyclo C-12 material produced according to the process of Example IV of Canadian Patent 854,225 issued October 20, 1970 | 5 |
| Iso Bornyl Cyclohexyl Alcohol | 10 |
| Bonzyl Acetate | 25 |
| 2-n-Heptyl Cyclopentanone | 5 |
| Mixture of dihydro gamma ionone, dihydro beta ionone and dihydro alpha ionone produced according to Example I(A) | 30 |
| TOTAL | 383.3 |

The foregoing blend is evaluated and found to have a high degree of richness and persistence in its novel natural amber quality. This base composition can be admixed with aqueous ethanol, chilled and filtered to produce a finished cologne. The cologne so prepared has an excellent amber aroma leaning towards a woody amber note. The base composition can also be used to scent soap or other toilet goods such as lotion, aerosol, sprays and the like.

EXAMPLE IV

The reaction product of Example I(B) is incorporated into a cologne having a concentration of 2.5% in 80% aqueous ethanol; and into a handkerchief perfume in a concentration of 20% (in 95% ethanol). The use of the reaction product of Example I(B) affords a distinct and definite warm, woody, earthy aroma to the handkerchief perfume and to the cologne.

EXAMPLE V

The following perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petitgrain SA | 20 |
| Bergamot Oil | 30 |
| Alpha Methyl Ionone | 25 |
| Mixture of isomers of 1', 2', 3', 4', 5', 6', 7', 8'-octahydro-2', 3', 8', 8'-tetramethyl-2'-acetonaphthones produced by the process of Example II (prior to GLC separation) of U.S. Pat. No. 3,911,018 | 10 |
| Cyclized Bicyclo C-12 material produced according to the process of Example IV of Canadian Patent 854,225 issued October 20, 1970 | 5 |
| Iso Bornyl Cyclohexyl Alcohol | 10 |
| Benzyl Acetate | 25 |
| 2-n-Heptyl Cyclopentanone | 5 |
| Mixture of dihydro gamma ionone, dihydro beta ionone and dihydro alpha ionone produced according to Example I(B) | 30 |
| TOTAL | 383.3 |

The foregoing blend is evaluated and found to have a high degree of richness and persistence in its novel natural amber quality. This base composition can be admixed with aqueous ethanol, chilled and filtered to produce a finished cologne. The cologne so prepared has an excellent amber aroma leaning towards a woody amber note. The base composition can also be used to scent soap or other toilet goods such as lotion, aerosol, sprays and the like.

What is claimed is:

1. A mixture of three oxazo derivatives of dihydro ionone derivatives defined by the generic structure:

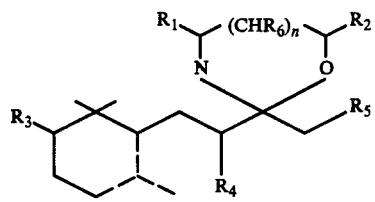

wherein one of the dashed lines is a carbon carbon double bond and the other two dashed lines are carbon carbon single bonds and n is 0 or 1; $R_1$, $R_2$ and $R_6$ are each the same or different and each represents hydrogen or $C_1$–$C_3$ lower alkyl; and $R_3$, $R_4$ and $R_5$ are each the same or different and each represents hydrogen or methyl, wherein in said mixture, the only difference among the derivatives is in the position of the carbon-to-carbon double bond.

2. The mixture of oxazo derivatives of claim 1 wherein each of $R_1$, $R_2$, $R_3$, $R_4$, $R_5$ and $R_6$ are hydrogen and n is 0 defined according to the structure:

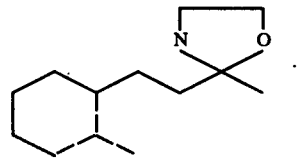

wherein one of the dashed lines is a carbon carbon double bond and the other two dashed lines are carbon carbon single bonds.

3. A cyclic oxazo derivative of geranyl acetone having the structure:

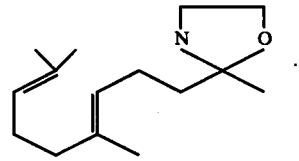

* * * * *

UNITED STATES PATENT AND TRADEMARK OFFICE
CERTIFICATE OF CORRECTION

PATENT NO. : 4,129,569

DATED : December 12, 1978

INVENTOR(S) : William L. Schreiber, James N. Siano and John B. Hall

It is certified that error appears in the above—identified patent and that said Letters Patent are hereby corrected as shown below:

Title page, right-hand column, line 3: the structure:

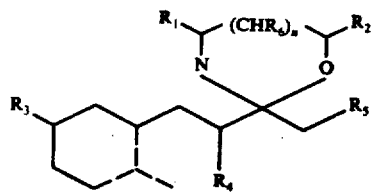

should be replaced with the structure:

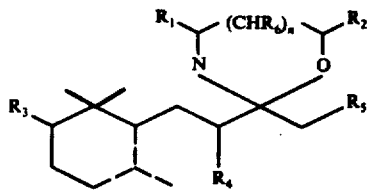

UNITED STATES PATENT AND TRADEMARK OFFICE
CERTIFICATE OF CORRECTION

PATENT NO. : 4,129,569
DATED : December 12, 1978
INVENTOR(S) : William L. Schreiber, James N. Siano and John B. Hall It is certified that error appears in the above-identified patent and that said Letters Patent are hereby corrected as shown below:

Column 14, line 25: the structure:

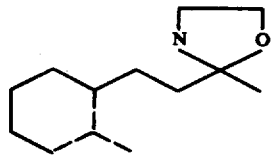

should be replaced with the structure:

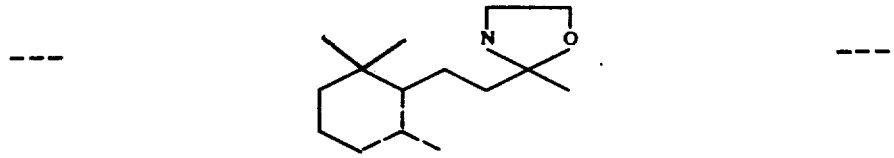

Signed and Sealed this

Fourth Day of March 1980

[SEAL]

Attest:

SIDNEY A. DIAMOND

Attesting Officer

Commissioner of Patents and Trademarks